US009084724B2

(12) United States Patent
Shirao et al.

(10) Patent No.: US 9,084,724 B2
(45) Date of Patent: Jul. 21, 2015

(54) WATER-IN-OIL TYPE EMULSION SUNSCREEN COSMETICS

(71) Applicant: Shiseido Co., Ltd., Chuo-ku, Tokyo (JP)

(72) Inventors: Masayuki Shirao, Yokohama (JP);
Kazuhiro Yamaguchi, Yokohama (JP);
Takashi Matsui, Yokohama (JP);
Norinobu Yoshikawa, Yokohama (JP);
Yuki Nomura, Yokohama (JP)

(73) Assignee: SHISEIDO CO., LTD., Tokyo (JP)

( * ) Notice: Subject to any disclaimer, the term of this patent is extended or adjusted under 35 U.S.C. 154(b) by 0 days.

(21) Appl. No.: 14/195,647

(22) Filed: Mar. 3, 2014

(65) Prior Publication Data
US 2014/0178481 A1 Jun. 26, 2014

Related U.S. Application Data

(62) Division of application No. 12/279,762, filed as application No. PCT/JP2007/053043 on Feb. 20, 2007, now abandoned.

(30) Foreign Application Priority Data

Feb. 20, 2006 (JP) ................. 2006-043215

(51) Int. Cl.
A61K 8/27 (2006.01)
A61Q 17/04 (2006.01)
A61K 8/02 (2006.01)
A61K 8/06 (2006.01)
A61K 8/25 (2006.01)
A61K 8/40 (2006.01)
A61K 8/41 (2006.01)
A61K 8/58 (2006.01)
A61K 8/73 (2006.01)

(52) U.S. Cl.
CPC ............... *A61K 8/0245* (2013.01); *A61K 8/06* (2013.01); *A61K 8/064* (2013.01); *A61K 8/25* (2013.01); *A61K 8/27* (2013.01); *A61K 8/40* (2013.01); *A61K 8/416* (2013.01); *A61K 8/585* (2013.01); *A61K 8/738* (2013.01); *A61Q 17/04* (2013.01)

(58) Field of Classification Search
CPC ................................ A61Q 17/04; A61K 8/25
USPC ............................................... 424/59
See application file for complete search history.

(56) References Cited

U.S. PATENT DOCUMENTS

| 5,827,508 | A | 10/1998 | Tanner et al. |
| 5,989,528 | A | 11/1999 | Tanner et al. |
| 6,153,174 | A | 11/2000 | Sperling et al. |
| 6,153,176 | A | 11/2000 | Kaleta et al. |
| 6,238,650 | B1 | 5/2001 | Lapidot et al. |
| 6,936,241 | B2 * | 8/2005 | Yamada et al. ............ 424/59 |
| 2003/0180232 | A1 | 9/2003 | Ishii et al. |
| 2004/0151673 | A1 | 8/2004 | Josso |
| 2007/0264292 | A1 | 11/2007 | Kurosawa et al. |
| 2009/0017081 | A1 | 1/2009 | Takakura et al. |
| 2009/0041817 | A1 | 2/2009 | Takakura et al. |

FOREIGN PATENT DOCUMENTS

| FR | 2882651 | 9/2006 |
| JP | 10-120543 | 5/1998 |
| JP | 2001-335410 | 12/2001 |
| JP | 2002-521417 | 7/2002 |
| JP | 2004-168781 | 6/2004 |
| JP | 2005-206573 | 8/2005 |
| JP | 2005-232068 | 9/2005 |
| JP | 2006-335654 | 12/2006 |
| WO | 98/13016 | 4/1998 |
| WO | 00/72806 | 12/2000 |
| WO | 02/03950 A2 | 1/2002 |
| WO | 02/03951 A2 | 1/2002 |
| WO | 02/22098 | 3/2002 |
| WO | 2005/079789 | 9/2005 |

OTHER PUBLICATIONS

Extended European Search Report dated Aug. 2, 2012, Application No. 07737302, Applicant—Shiseido Company, Limited, five pages.
AGS Si-Tech "Fine Silica Products," <http://www.agcce.com/brochurespdfs/sales/Silica.pdf>, Jan. 2011, four pages.
Personal Care Magazine, "Suppliers' Strengths to be Highlighted at PCIA 2006," <http://www.personalcaremagazine.com/Print.aspx?Story=711>, Jan. 2006, five pages.
Derwent Abstract for JP Publication No. 2005232068 published Sep. 2, 2005, five pages.
English translation of JP 2001-3355410, published Dec. 4, 2001, 25 pages.
Japanese Patent Abstract for JP Publication No. 2006-335654 published Dec. 14, 2006, 12 pages.
Partial English translation of the specification for JP Publication No. 2005-206573 published Aug. 4, 2005, four pages.
Partial English translation of the specification for FR Publication No. 2882651 published Sep. 8, 2006, four pages.
International Search Report for corresponding PCT/JP2007/053043 mailed May 29, 2007, two pages.

* cited by examiner

*Primary Examiner* — Gina Justice
(74) *Attorney, Agent, or Firm* — Rankin, Hill & Clark LLP

(57) ABSTRACT

The present invention provides water-in-oil type emulsion sunscreen cosmetics that achieve an excellent UV blocking effect, and have excellent effects in the prevention and inhibition of discoloration (discoloration to red). The water-in-oil emulsion sunscreen cosmetic according to the present invention is characterized by comprising: (a) octocrylene; (b) hydrophobized zinc oxide; (c) cationic surfactant; and (d) silica.

14 Claims, No Drawings

WATER-IN-OIL TYPE EMULSION SUNSCREEN COSMETICS

RELATED APPLICATIONS

This application claims the priority of Japanese Patent Application No. 2006-043215 filed on Feb. 20, 2006, which are incorporated herein by reference.

FIELD OF THE INVENTION

The present invention relates to water-in-oil type emulsion sunscreen cosmetics. In particular, the present invention relates to water-in-oil type emulsion sunscreen cosmetics that have an excellent UV protection capability and have excellent effects in the prevention and inhibition of discoloration (discoloration to red).

BACKGROUND OF THE INVENTION

Generally, in order to block UV radiation to the skin and achieve high SPF (Sun Protection Factor) values, UV absorbers or UV scattering agents (zinc oxide etc.) are blended in sunscreen cosmetics (refer to patent literatures 1 and 2, for example).

It is generally known that the improvement in formulation stability, improvement in removability, and the improvement in powder dispersibility are made by blending cationic surfactants into cosmetics.

Octocrylene is an all-purpose UV absorber. However, there is a problem in that the appearance of the formulation turns extremely red when a hydrophobized UV scattering agent (especially zinc oxide) is used in combination with a cationic surfactant in water-in-oil type sunscreen cosmetics.

Patent Literature 1: Japanese Unexamined Patent Publication No. H10-120543 (paragraph numbers [0032], [0041], [0045], etc.)

Patent Literature 2: PCT Japanese Translation Patent Publication No. 2002-521417 (claim section etc.)

DISCLOSURE OF THE INVENTION

Problem to be Solved by the Invention

The object of the present invention is to provide water-in-oil type emulsion sunscreen cosmetics that solve the above-described problem, achieve an excellent UV blocking effect, and have excellent effects in the prevention and inhibition of discoloration (discoloration to red).

Means to Solve the Problem

The present inventors have diligently studied to solve the above-described problem. As a result, the present inventors have found that an excellent UV blocking effect and the prevention and inhibition effects of red discoloration could be achieved by blending silica into a system where octocrylene, a hydrophobized UV scattering agent (especially zinc oxide), and a cationic surfactant are blended, thus leading to completion of the present invention.

The present invention provides water-in-oil type emulsion sunscreen cosmetics comprising: (a) octocrylene; (b) hydrophobized zinc oxide; (c) cationic surfactant; and (d) silica.

The present invention provides the above-described water-in-oil type emulsion sunscreen cosmetics comprising said component (c), with which component (b) is surface-coated.

The present invention provides the above-described water-in-oil type emulsion sunscreen cosmetics wherein the blending amount of said component (a) is 0.2 to 15% by mass.

The present invention provides the above-described water-in-oil type emulsion sunscreen cosmetics wherein the blending amount of said component (b) is 0.2 to 30% by mass.

The present invention provides the above-described water-in-oil type emulsion sunscreen cosmetics further comprising: (e) 0.01 to 20% by mass of silicone surfactant.

According to the present invention, water-in-oil type emulsion sunscreen cosmetics that can satisfactorily achieve an excellent UV blocking effect and have excellent effects in the prevention and inhibition of discoloration (discoloration to red) can be provided.

Hereinafter, the water-in-oil type emulsion sunscreen cosmetics of the present invention will be described in detail.

BEST MODE FOR CARRYING OUT THE INVENTION

Octocrylene (another name: 2-cyano-3,3-diphenyl-2-propenoic acid 2-ethylhexyl ester), which is component (a) used in the present invention, is a UV protection agent, and it is a publicly known material. Octocrylene can normally be prepared by the esterification reaction of cyanoacetic acid and 2-ethylhexanol in a solvent (for example, cyclohexane) to 2-ethylhexyl cyanoacetate and by the subsequent condensation reaction of the obtained 2-ethylhexyl cyanoacetate with benzophenone. In the actual preparation, octocrylene may be produced in a state that 2-ethylhexyl cyanoacetate is not completely used in the condensation process and 2-ethylhexyl cyanoacetate is partially left. In the present invention, the lower the concentration of 2-ethylhexyl cyanoacetate in octocrylene, the more desirable. The concentration is preferably 400 ppm or lower, more preferably 200 ppm or lower, and further more preferably 100 ppm or lower. The most desirable concentration of 2-ethylhexyl cyanoacetate is zero. If the concentration of 2-ethylhexyl cyanoacetate contained in octocrylene is high, it tends to be more difficult to achieve the prevention and inhibition effects of discoloration (discoloration to red), which are the effects of the present invention.

Component (a) includes, for example, commercial products such as "Uvinul N539" (BASF) or "Parsol 340" (DSM Nutrition Japan K.K.), and they can be used desirably.

The blending amount of component (a) is 0.2 to 15% by mass with respect to the cosmetics of the present invention, preferably 0.5 to 10% by mass, and more preferably 1 to 7% by mass. If the blending amount is less than 0.2% by mass, a satisfactory UV protection capability cannot be achieved. On the other hand, if the blending amount exceeds 15% by mass, a high tendency of discoloration (discoloration to red) is observed and there is a concern with usability deterioration such as stickiness and an oily feeling.

Hydrophobized zinc oxide, which is used as component (b), is a UV scattering agent, and it can effectively be dispersed in the oil phase (outer phase) after hydrophobizing treatment.

From the stand point of a UV-scattering effect, zinc oxide is preferably prepared into fine particles. The average primary particle size of zinc oxide fine particles can be about 1 to 50 nm. However, the size is not limited to this size.

The method for hydrophobizing treatment is not limited in particular, and a publicly known method can be used for treatment. Examples of hydrophobizing agents include, but not limited in particular, metallic soap (for example, aluminum stearate and aluminum laurate), fatty acid dextrin, trimethylsiloxane, fluorine-modified trimethylsiloxane, methylphenylsiloxane, fluorine-modified methylphenylsiloxane, low-viscosity to high-viscosity oily polysiloxanes such as dimethylpolysiloxane (=dimethicone), methylpolysiloxane (=methicone), diphenylpolysiloxane, and methylphenylpolysiloxane; gummy polysiloxane, methylhydrogenpolysiloxane, fluorine-modified methylhydrogenpolysiloxane, organic-modified silanes such as methyltrichlorosilane, ethyltrichlorosilane, ethyltrialkoxysilane, propyltrichlorosilane, propyltrialkoxysilane, hexyltrichlorosilane, hexyltrialkoxysilane, methyltrialkoxysilane, hexamethyldisilane, dimethyldichlorosilane, dimethyldialkoxysilane, trimethylchlorosilane, trimethylalkoxysilane, long-chain alkyltrichlorosilane, and long-chain alkyltriethoxysilane; or their fluorine-substituted compounds, amino-modified polysiloxane, fluorine-modified polysiloxane, and fluoroalkyl phosphate. However, the hydrophobizing agent is not limited by these examples. In hydrophobizing treatment, it is preferable to use 3 to 90% by mass hydrophobizing agent, for coating, with respect to zinc oxide (base body).

Examples of hydrophobized zinc oxide include metallic soap-treated zinc oxide, for example by aluminum stearate; fatty acid-dextrin treated zinc oxide, for example by cyclodextrin-fatty acid ester; amino acid treated zinc oxide; oily polysiloxane treated zinc oxide, for example by methylhydrogenpolysiloxane, methylhydrogenpolysiloxane/dimethylpolysiloxane copolymer, methicone, or dimethicone; fluorine-treated zinc oxide, for example by perfluoroalkyl phosphate; and silane coupling agent treated zinc oxide, for example by octyltriethoxysilane.

The blending amount of component (b) is 0.2 to 30% by mass with respect to the cosmetics of the present invention, preferably 1 to 25% by mass, and more preferably 10.1 to 25% by mass. If the blending amount is less than 0.2% by mass, a satisfactory UV protective effect cannot be achieved. On the other hand, if the blending amount exceeds 30% by mass, there is a concern with the discoloration (discoloration to red) and usability deterioration as typified by smoothlessness.

The cationic surfactant, which is component (c), is not limited in particular so far as the cationic surfactant can be generally used in cosmetics. Examples include stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP(25) diethylmethyl cation, POP (40) diethylmethyl cation, C12 diamidopropylmethylamine, C14 diamidopropylmethylamine, C16 diamidopropylmethylamine, C18 diamidopropylmethylamine, iso-C18 diamidopropylmethylamine, di-C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di-C18 amidoethylethylhydroxy cation, di-C16 amidoethylethylhydroxy cation, di-C18 dimethylammonium salt, C18 dimethylbenzylammonium salt, perfluorotrimethylammonium salt, and diacylamidoethylethylhydroxy cation. However, the cationic surfactant is not limited by these examples.

The especially desirable component (c) is distearyldimethylammonium salt, dihexadecyldimethylammonium salt, ditetradecyldimethylammonium salt, didodecyldimethylammonium salt, stearyltrimethylammonium chloride, hexadecyltrimethylammonium chloride, tetradecyltrimethylammonium chloride, or dodecyltrimethylammonium chloride. One or more of component (c) can be used.

Silica, which is component (d), is silicon dioxide (silicic anhydride). Treated silicas such as dimethylsilanized silicic anhydride and trimethylsilanized silicic anhydride can also be used. The silica can be of any shape; the shape can be spherical and porous, plate-like and nonporous, particulate, rod-like and porous, or spherical and nonporous, and there is no particular restriction. However, spherical porous silica, particulate silica, or rod-like porous silica is preferably used. Component (d) includes, for example, commercial products such as "Sunsphere L-51" (manufactured by Asahi Glass Co., Ltd.), "Chemiselen" (manufactured by Sumitomo Chemical Co., Ltd.), "Aerosil 200" (manufactured by Nippon Aerosil Co., Ltd.), "Spherical Silica P1500" (manufactured by Catalysts & Chemicals Ind. Co., Ltd.), and "Mesoporous Silica", and these can be used desirably.

In the present invention, the blending mode of component (b), component (c), and component (d) is not limited in particular. Examples include:

(i) Blending mode in which component (b), component (c), and component (d) are individually blended.

(ii) Blending mode in which the hydrophobized and cation-treated zinc oxide, which is obtained by treating component (b) with component (c), is blended with component (d).

(iii) Blending mode in which the hydrophobized, cation-treated, and silica-coated zinc oxide, which is obtained by coating, with component (d), the hydrophobized and cation-treated zinc oxide obtained by treating component (b) with component (c), is blended.

(iv) Blending mode in which the hydrophobized silica-coated zinc oxide, which is obtained by treating component (b) with component (d), is blended with component (c).

(v) Blending mode in which untreated zinc oxide is silica-coated with component (d), and this silica-coated zinc oxide is hydrophobized with a hydrophobizing agent and cation-treated with component (c). The blending mode is not limited by the above-described examples. The blending of component (d) may be achieved by silica-coated powders obtained by coating the surface of powders, except for component (b), with silica.

The blending amounts of component (c) and component (d) are as follows.

When component (c) is blended in the mode of individual addition instead of blending the powder treated therewith, the blending amount of component (c) in cosmetics is preferably 0.0001 to 10% by mass and more preferably 0.001 to 1% by mass. When component (c) is used as the surface coating of component (b), the blending amount of component (c) is preferably 0.5 to 10% by mass with respect to zinc oxide (base body). If the blending amount of component (c) is too small, the formulation stability, removability, and the powder dispersibility tend to be become lower. On the other hand, if the blending amount of component (c) is too large, the discoloration may not be inhibited even by blending component (d).

When component (d) is blended in the mode of individual addition instead of blending the powder treated therewith, the blending amount of component (d) in cosmetics is preferably 0.1 to 20% by mass and more preferably 0.5 to 10% by mass. When component (d) is used as the surface coating of component (b) or as the surface coating of component (b) that has been coated with component (c), the blending amount of component (d) is preferably 0.1 to 20% by mass with respect to zinc oxide (base body). If the blending amount of component (d) is too small, the dispersion stability tends to become lower. On the other hand, if the blending amount of component (d) is too large, the UV protection capability tends to become lower. When component (d) and component (c) are individually blended, it is desirable to blend component (d) in a mass ratio of 0.01:6 or higher with respect to component (c). In this case, if the blending amount of component (d) is too small, the discoloration to red may take place.

An example of a production method when both hydrophobizing treatment and cation treatment are performed on zinc oxide (base body) is described below. However, the method is not limited to this method. Into a solvent, 3 to 90% by mass of various hydrophobizing agents and 0.5 to 10% by mass of cationic surfactants with respect to the powder (base body) are added and dissolved. Subsequently, the powder (base body) is added and stirred for 1 hour at room temperature. After the completion of stirring, the solvent removal, drying, and pulverization are carried out to obtain the desired modified powder. As a solvent, methyl alcohol, ethyl alcohol, and isopropyl alcohol, into which various hydrophobizing agents and cationic surfactants can be dissolved, may be used. In particular, isopropyl alcohol is desirable.

The production can also be achieved by treating a commercial hydrophobized powder with a cationic surfactant.

The amounts of coating of a hydrophobizing agent and a cationic surfactant are preferably in the mass ratio of 1:1 to 9:1. If the rate of the cationic surfactant is larger than the above-described range, the water resistance may become poor. If the rate is smaller, the dispersibility and removability may become poor.

In the present invention, it is desirable that a (e) silicone surfactant is further blended as an emulsifying agent. The silicone surfactant is not limited in particular so far as it is usable in water-in-oil emulsion systems. Examples include poly(oxyethylene/oxypropylene)methylpolysiloxane copolymer, polyoxyethylene methylpolysiloxane copolymer, silicone-chain branched-type methylpolysiloxane copolymer, alkyl-chain branched-type polyoxyethylene methylpolysiloxane copolymer, alkyl-chain/silicone-chain branched-type polyoxyethylene methylpolysiloxane copolymer, crosslinked-type polyoxyethylene methylpolysiloxane, alkyl-containing crosslinked-type polyoxyethylene methylpolysiloxane, branched-type polyglycerin-modified silicone, crosslinked-type polyglycerin-modified silicone, alkyl-containing crosslinked-type polyglycerin-modified silicone, and alkyl group branched-type polyglycerin-modified silicone. However, the silicone surfactant is not limited to these.

Examples of the above-described poly(oxyethylene/oxypropylene)methylpolysiloxane copolymers include PEG/PPG-20/22 butyl ether dimethicone ("KF-6012", manufactured by Shin-Etsu Chemical Co., Ltd.), PEG/PPG-20/20 dimethicone ("BY22-008M", manufactured by Toray Dow Corning Silicone Co., Ltd.), lauryl PEG/PPG-18 methicone ("5200 Formulation Aid", manufactured by Dow Corning Toray Co., Ltd.), PEG/PPG-19/19 dimethicone ("5330 Fluid", manufactured by Dow Corning Toray Co., Ltd.), and PEG/PPG-15/15 dimethicone ("5330 Fluid", manufactured by Dow Corning Toray Co., Ltd.).

Examples of polyoxyethylene methylpolysiloxane copolymers include PEG-11 methyl ether dimethicone ("KF-6011", manufactured by Shin-Etsu Chemical Co., Ltd.), PEG-9 dimethicone ("KF-6013", manufactured by Shin-Etsu Chemical Co., Ltd.), PEG-3 dimethicone ("KF-6015", manufactured by Shin-Etsu Chemical Co., Ltd.), PEG-9 methyl ether dimethicone ("KF-6016", manufactured by Shin-Etsu Chemical Co., Ltd.), PEG-10 dimethicone ("KF-6017", manufactured by manufactured by Shin-Etsu Chemical Co., Ltd.), PEG-11 methyl ether dimethicone ("KF-6018", manufactured by Shin-Etsu Chemical Co., Ltd.), PEG-9 dimethicone ("KF-6019", manufactured by Shin-Etsu Chemical Co., Ltd.), and PEG-12 dimethicone ("SH3771 M", "SH3772M", "SH3773M", "SH3775M" etc., manufactured by Dow Corning Toray Co., Ltd.).

Examples of silicone-chain branched-type methylpolysiloxane copolymers include PEG-9 polydimethylsiloxyethyl dimethicone ("KF-6028", manufactured by Shin-Etsu Chemical Co., Ltd.).

Examples of alkyl-chain branched-type polyoxyethylene methylpolysiloxane copolymers include PEG/PPG-10/3 oleyl ether dimethicone ("KF-6026", manufactured by Shin-Etsu Chemical Co., Ltd.).

Examples of alkyl-chain/silicone-chain branched-type polyoxyethylene methylpolysiloxane copolymers include lauryl PEG-9 polydimethylsiloxyethyl dimethicone ("KF-6038", manufactured by Shin-Etsu Chemical Co., Ltd.).

Examples of crosslinked-type polyoxyethylene methylpolysiloxanes include dimethicone/(PEG-10/15) crosspolymer ("KSG-210", manufactured by Shin-Etsu Chemical Co., Ltd.) and cyclomethicone/(PEG-12 dimethicone) crosspolymer ("9011 Silicone Elastomer Blend", manufactured by Toray Dow Corning Silicone Co., Ltd.).

Examples of alkyl-containing crosslinked-type polyoxyethylene methylpolysiloxanes include mineral oil/PEG-15 lauryl dimethicone crosspolymer ("KSG-310", manufactured by Shin-Etsu Chemical Co., Ltd.), isododecane/PEG-15 lauryl dimethicone crosspolymer ("KSG-320", manufactured by Shin-Etsu Chemical Co., Ltd.), trioctanoin/PEG-15 lauryl dimethicone crosspolymer ("KSG-330", manufactured by Shin-Etsu Chemical Co., Ltd.), and squalane/PEG-15 lauryl dimethicone crosspolymer/PEG-10 lauryl dimethicone crosspolymer ("KSG-340", manufactured by Shin-Etsu Chemical Co., Ltd.).

Examples of branched-type polyglycerin-modified silicones include polyglyceryl-3 disiloxane dimethicone ("KF-6100", manufactured by Shin-Etsu Chemical Co., Ltd.) and polyglyceryl-3 polydimethylsiloxyethyl dimethicone ("KF-6104", manufactured by Shin-Etsu Chemical Co., Ltd.).

Examples of crosslinked-type polyglycerin-modified silicones include dimethicone/(dimethicone/polyglycerin-3) crosspolymer ("KSG-710", manufactured by Shin-Etsu Chemical Co., Ltd.).

Examples of alkyl-containing crosslinked-type polyglycerin-modified silicones include mineral oil/(lauryl dimethicone/polyglycerin-3) crosspolymer ("KSG-810", manufactured by Shin-Etsu Chemical Co., Ltd.), isododecane/(lauryl dimethicone/polyglycerin-3) crosspolymer ("KSG-820, manufactured by Shin-Etsu Chemical Co., Ltd."), trioctanoin/(lauryl dimethicone/polyglycerin-3) crosspolymer ("KSG-830", manufactured by Shin-Etsu Chemical Co., Ltd.), and squalane/(lauryl dimethicone/polyglycerin-3) crosspolymer ("KSG-840", manufactured by Shin-Etsu Chemical Co., Ltd.).

Examples of alkyl group branched-type polyglycerin-modified silicones include lauryl polyglyceryl-3 polydimethylsiloxyethyl dimethicone ("KF-6105", manufactured by Shin-Etsu Chemical Co., Ltd.).

Among them, polyoxyethylene methylpolysiloxane copolymer, poly(oxyethylene/oxypropylene)methylpolysiloxane copolymer, silicone-chain branched-type methylpolysiloxane copolymer, and alkyl-chain/silicone-chain branched-type polyoxyethylene methylpolysiloxane copolymer are desirably used.

The blending amount of component (e) in the sunscreen cosmetics of the present invention is preferably 0.01% by mass at the lower limit, more preferably 0.1% by mass or higher, and further more preferably 0.5% by mass or higher. The upper limit is preferably 20% by mass or lower and more preferably 10% by mass or lower. If the blending amount is less than 0.01% by mass, the stability of cosmetics tends to become poorer. On the other hand, if the blending amount largely exceeds 20% by mass, a sticky feeling is generated and the feeling in use tends to become poorer.

In the water-in-oil type emulsion sunscreen cosmetics of the present invention, it is preferred that the oil phase (outer phase) is 40 to 80% by mass and the water phase (inner phase) is 20 to 60% by mass.

In the cosmetics of the present invention, in addition to the above-described components, other components normally be used in cosmetics can be blended as necessary so far as the objectives and effects of the present invention are not undermined. Examples of these components include water-soluble polymers, oil-soluble polymers, polymer powders, emulsifying agents (other than the above-described component (e)), waxes, alcohols, liquid fats, ester oils, hydrocarbon oils, silicone oils, fatty acids, higher alcohols, fatty acid esters, drugs, UV absorbers (other than the above-described component (a)), UV scattering agents (other than the above-described component (b)), and organic-modified clay minerals. However, the components are not limited by these examples.

Examples of water-soluble polymers include a homopolymer and copolymers of 2-acrylamido-2-methyl propane sulfonic acid (hereinafter abbreviated as "AMPS"). The copolymer comprises comonomers such as vinylpyrrolidone, acrylamide, sodium acrylate, and hydroxyethyl acrylate. Examples include AMPS homopolymer, vinylpyrrolidone/AMPS copolymer, dimethylacrylamide/AMPS copolymer, acrylamide/AMPS copolymer, and sodium acrylate/AMPS copolymer.

Further examples include carboxyvinyl polymer, ammonium polyacrylate, sodium polyacrylate, sodium acrylate/alkyl acrylate/sodium methacrylate/alkyl methacrylate copolymer, carrageenan, pectin, mannan, curdlan, chondroitin sulfate, starch, glycogen, gum arabic, sodium hyaluronate, tragacanth gum, xanthan gum, mucoitin sulfate, hydroxyethyl guar gum, carboxymethyl guar gum, guar gum, dextran, kerato sulfate, locust bean gum, succinoglucan, chitin, chitosan, carboxymethyl chitin, and agar.

Examples of oil-soluble polymers include trimethylsiloxysilicate, alkyl-modified silicone, and polyamide-modified silicone.

Examples of polymer powders include dimethicone crosspolymer, (dimethicone/vinyldimethicone) crosspolymer, polymethylsilsesquioxane, polyethylene, and polymethylmethacrylate.

Examples of waxes include beeswax, candelilla wax, carnauba wax, lanolin, lanolin oil, and jojoba wax.

Examples of emulsifying agents (other than the above-described component (e)) include glycerin fatty acid ester, polyglycerin fatty acid ester, polyoxyethylene glycerin fatty acid ester, sorbitan fatty acid ester, and polyoxyethylene sorbitan fatty acid ester.

Examples of alcohols include lower alcohols such as ethanol and isopropanol; higher alcohols such as isostearyl alcohol, octyldodecanol, and hexyldecanol; and polyhydric alcohols such as ethylene glycol, propylene glycol, 1,3-butylene glycol, dipropylene glycol, and polybutylene glycol.

Examples of liquid fats include avocado oil, camellia oil, turtle oil, macadamia nut oil, corn oil, mink oil, olive oil, rapeseed oil, egg oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japanese tung oil, jojoba oil, germ oil, and triglycerin.

Examples of ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, acetylated lanolin, isocetyl stearate, isocetyl isostearate, isononyl isononate, cholesteryl 12-hydroxystearate, ethylene glycol di-2-ethylhexanoate, dipentaerythritol fatty acid ester, N-alkylglycol monoisostearate, neopentyl glycol dicaprylate, diisostearyl malate, glyceryl di-2-heptylundecanoate, trimethylolpropane tri-2-ethylhexanoate, trimethylolpropane triisostearate, pentaerythritol tetra-2-ethylhexanoate, glyceryl tri-2-ethylhexanoate, glyceryl trioctanoate, glyceryl triisopalmitate, trimethylolpropane triisostearate, cetyl 2-ethylhexanoate, 2-ethylhexyl palmitate, glyceryl trimyristate, glyceride tri-2-heptylundecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of hydrocarbon oils include liquid paraffin, ozokerite, squalane, pristane, paraffin, ceresin, squalene, petrolatum, microcrystalline wax, polyethylene wax, and Fischer-Tropsch wax.

Examples of silicon oils include dimethylpolysiloxane, octamethylsiloxane, decamethyltetrasiloxane, methylhydrogenpolysiloxane, methylphenylpolysiloxane, hexamethylcyclotrisiloxane, octamethylcyclotetrasiloxane, and decamethylcyclopentasiloxane.

Examples of fatty acids include lauric acid, myristic acid, palmitic acid, stearic acid, behenic acid, and arachidonic acid.

Examples of higher alcohols include lauryl alcohol, myristyl alcohol, cetyl alcohol, stearyl alcohol, behenyl alcohol, arachyl alcohol, batyl alcohol, chimyl alcohol, carnaubyl alcohol, ceryl alcohol, koryanyl alcohol, myricyl alcohol, lacceryl alcohol, elaidyl alcohol, isostearyl glyceryl ether, octyl alcohol, triacontyl alcohol, cerakyl alcohol, cetostearyl alcohol, oleyl alcohol, lanolin alcohol, hydrogenated lanolin alcohol, hexyldecanol, and octyldecanol.

Examples of fatty acid esters include myristyl myristate, cetyl palmitate, cholesteryl stearate, and 2-octyldodecyl beeswax fatty acid.

Examples of drugs include L-ascorbic acid and its salt derivatives, glycyrrhizic acid and its derivatives such as dipotassium glycyrrhizate and monoammonium glycyrrhizate, glycyrrhetinic acid and its derivatives such as stearyl glycyrrhetinate, allantoin, tranexamic acid and its salt derivatives, alkoxysalicylic acid and its salt derivatives, glutathione and its salt derivatives, allantoin, and azulene.

Examples of UV absorbers (other than the above-described component (a)) include cinnamic acid derivatives such as ethylhexyl methoxycinnamate, isopropyl methoxycinnamate, and isoamyl methoxycinnamate; PABA derivatives such as para-aminobenzoic acid (hereinafter abbreviated as "PABA"), ethyl PABA, ethyl dihydroxypropyl PABA, ethylhexyl dimethyl PABA, and glyceryl PABA; salicylic acid derivatives such as homosalate, ethylhexyl salicylate, dipropylene glycol salicylate, and TEA salicylate; benzophenone derivatives such as benzophenone-1, benzophenone-2, benzophenone-3 or oxybenzone, benzophenone-4, benzophenone-5, benzophenone-6, benzophenone-8, benzophenone-9, and benzophenone-12; benzylidene camphor derivatives such as 3-benzylidene camphor, 4-methylbenzylidene camphor, benzylidene camphor sulfonic acid, camphor benzalkonium methosulfate, terephthalylidene dicamphor sulfonic acid, and polyacrylamidomethyl benzylidene camphor; triazine derivatives such as anisotriazine, ethylhexyl triazone, diethylhexyl butamido triazone, and 2,4,6-tris(diisobutyl 4'-aminobenzalmalonate)-s-triazine; phenylbenzimidazole derivatives such as disodium phenyldibenzimidazole tetrasulfonate; phenylbenzotriazol derivatives such as drometrizole trisiloxane and methylene bis-benzotriazolyl tetramethylbutylphenol; anthranilic derivatives such as menthyl anthranilate; imidazoline derivatives such as ethylhexyl dimethoxybenzylidene dioxoimidazoline propionate; benzalmalonate derivatives such as polyorganosiloxanes with benzalmalonate functional groups; and 4,4-diarylbutadiene derivatives such as 1,1-dicarboxy(2,2'-dimethylpropyl)-4,4-diphenylbutadiene.

Examples of UV scattering agents (other than the above-described component (b)) include hydrophobized inorganic pigments such as titanium dioxide, kaolin, and calcium carbonate.

Examples of organic-modified clay minerals include quaternary ammonium cation modified clay minerals.

The water-in-oil type emulsion sunscreen cosmetics of the present invention include products such as emulsion type and cream type. These products can be prepared by the conventional method by mixing the above-described essential components and the components that are normally blended in cosmetics.

Hereinafter, the present invention will be described in further detail with reference to examples. However, the present invention is not limited by the following examples. All the blending amounts are shown in % by mass.

EXAMPLES

Before the examples are described, test methods and evaluation methods used in the present invention will be described.
[Prevention and Inhibition Effects of Red Discoloration]

After each sample was allowed to stand at 70° C. for 3 days, the appearance was visually evaluated.
(Evaluation)
○: No discoloration (discoloration to red) was observed.
○Δ: A slight discoloration (discoloration to red) was observed.
Δ: Some discoloration (discoloration to red) was observed.
ΔX: Appreciable discoloration (discoloration to red) was observed.
X: Discoloration (discoloration to red) was observed.
XX: Significant discoloration (discoloration to red) was observed.

Example 1

In a simple oil phase system, the prevention and inhibition effects of red discoloration were evaluated according to the above-described evaluation criteria. The evaluation was conducted, with the use of samples A to K of the below-described compositions, in relation to the blending/non-blending of respective components (a) to (d), system discoloration to red, and the prevention and inhibition effects of red discoloration. The results are shown in Table 1.

In Table 1, "octocrylene"$^{(*1)}$, in which the amount of 2-ethylhexyl cyanoacetate is about 1000 ppm, and "octocrylene"$^{(*2)}$, in which the amount of 2-ethylhexyl cyanoacetate is about 100 ppm, were used. They were the same in examples in Table 2 and examples in tables below Table 2.

In Table 1, the percentages (mass ratio) of component (b) and component (c) in "(6) hydrophobized (silane treatment)/cation-treated zinc oxide [component (b)+component (c)]" were about 98% by mass and about 2% by mass, respectively.

The percentages (mass ratio) of component (b) and component (d) in "(7) hydrophobized (silane treatment)/silica-coated zinc oxide [component (b)+component (d)]" were about 80% by mass and about 20% by mass, respectively.

The percentage (mass ratio) of component (d) in "(8) hydrophobized (silane treatment)/silica-coated titanium dioxide [component (d)]" was about 10% by mass. That is, the blending amount of component (d) in sample I was 1.5% by mass.

TABLE 1

| | Sample A (control) | Sample B | Sample C, D, E | Sample F, G, H | Sample I | Sample J | Sample K | Sample L | Sample M |
|---|---|---|---|---|---|---|---|---|---|
| (1) Decamethylcyclopentasiloxane | 65 | 50 | Balance | Balance | 35 | 35 | 65 | 50 | 50 |
| (2) Methylphenylpolysiloxane | 20 | 20 | 20 | 20 | 20 | 20 | 20 | 20 | 20 |
| (3) Octocrylene (*1) [component (a)] | 15 | 15 | 15 | 15 | 15 | 15 | — | — | — |
| (4) Octocrylene (*2) [component (a)] | — | — | — | — | — | — | — | 15 | 15 |
| (5) Hydrophobized (silane treatment) zinc oxide [component (b)] | — | 15 | — | — | — | — | — | — | — |
| (6) Hydrophobized (silane treatment)/cation-treated zinc oxide [component (b) + component (c)] | — | — | 5, 10, 15 | 15 | 15 | 15 | 15 | 15 | 15 |
| (7) Hydrophobized (silane treatment)/silica-coated zinc oxide [component (b) + component (d)] | — | — | — | — | — | 15 | — | — | — |
| (8) Hydrophobized (silane treatment)/silica-coated titanium dioxide [component (d)] | — | — | — | — | 15 | — | — | — | — |
| (9) Silica powder [component (d)] | — | — | — | 1, 3, 6 | — | — | — | — | 1 |
| Prevention and inhibition effects of red discoloration (at 70° C. for 3 days, visual evaluation) | ○ | ○ | X, XX, XX | ○, ○, ○ | ○ | ○ | ○ | ○Δ | ○ |

As is clear from the results in Table 1, sample A (control) containing component (a) but not containing components (b) and (c) did not discolor to red even without blending component (d). Sample B containing components (a) and (b) but not containing component (c) did not discolor to red even without component (d). Samples C to E containing components (a) to (c) but not containing component (d) discolored to red. However, samples F to H, in which component (d) was added to components (a) to (c), and samples I and J, in which component (d) was added by coating the powder therewith, did not discolor to red. As shown in sample K, when component (a) was not blended, the discoloration to red did not take place even when components (b) and (c) were blended. When octocrylene containing 100 ppm of 2-ethylhexyl cyanoacetate was used as component (a), the prevention and inhibition effects of red discoloration were better than when octocrylene containing 1000 ppm of 2-ethylhexyl cyanoacetate was used (comparison between sample E and sample L).

Example 2

For the case in that component (c) and component (d) are individually blended instead of blending the powder coated therewith, the blending amounts and the prevention effect of red discoloration were evaluated according to the above-described evaluation criteria. The results are shown in Tables 2 and 3.

In Table 2, the percentages (mass ratio) of component (b) and component (c) in "(5) hydrophobized (silane treatment)/cation-treated zinc oxide [component (b)+component (c)]" were about 98% by mass and about 2% by mass, respectively.

TABLE 2

|  | Sample X | Sample Y |
|---|---|---|
| (1) Decamethylcyclopentasiloxane | Balance | Balance |
| (2) Methylphenylpolysiloxane | 20 | 20 |
| (3) Octocrylene (*2) [component (a)] | 15 | 15 |
| (4) Hydrophobized (silane treatment) zinc oxide [component (b)] | — | 15 |
| (5) Hydrophobized (silane treatment)/cation-treated zinc oxide [component (b) + component (c)] | 15 | — |
| (6) Distearyldimethylammonium chloride [component (c)] | — | Table 3 |
| (7) Silica powder [component (d)] | — | Table 3 |
| Prevention and inhibition effects of red discoloration (at 70° C. for 3 days, visual evaluation) | X | Table 3 |

TABLE 3

| | Distearyldimethylammonium chloride [component (c)] (blending amounts in sample Y, in % by mass) | | | | | | |
|---|---|---|---|---|---|---|---|
| | 0 | 0.01 | 0.1 | 0.5 | 1 | 3 | 6 |
| | Prevention and inhibition effects of red discoloration (at 70° C. for 3 days, visual evaluation) | | | | | | |
| Silica powder [component (d)] (blending amounts in sample Y, in % by in mass) 0 | 0 | ○ | X | X | XX | XX | XX | XX |
| 1 | — | ΔX | X | XX | XX | XX | XX |
| 3 | — | ΔX | X | XX | XX | XX | XX |
| 6 | — | ○Δ | ΔX | XX | XX | XX | XX |
| 10 | — | ○Δ | — | — | — | — | — |

As shown in the results of Tables 2 and 3, the improvement in discoloration was observed by blending 6% by mass or higher component (d) to 0.01% by mass component (c).

Example 3

The discoloration of a system (sample Z) in which other powder components are blended instead of silica was evaluated according to the above-described evaluation criteria. The results are shown in Tables 4 and 5.

In Table 4, the percentages (mass ratio) of component (b) and component (c) in "(5) hydrophobized (silane treatment)/cation-treated zinc oxide [component (b)+component (c)]" were about 98% by mass and about 2% by mass, respectively.

TABLE 4

|  | Sample Z |
|---|---|
| (1) Decamethylcyclopentasiloxane | Balance |
| (2) Methylphenylpolysiloxane | 20 |
| (3) Octocrylene (*1) [component (a)] | 15 |
| (4) Hydrophobized (silane treatment) zinc oxide [component (b)] | — |
| (5) Hydrophobized (silane treatment)/cation-treated zinc oxide [component (b) + component (c)] | 15 |
| (6) Distearyldimethylammonium chloride [component (c)] | — |
| (7) Powder component shown in table 5 | 6 |
| Prevention and inhibition effects of red discoloration (at 70° C. for 3 days, visual evaluation) | Table 5 |

TABLE 5

| Powder component | Prevention and inhibition effects of red discoloration (at 70° C. for 3 days, visual evaluation) |
|---|---|
| Silicone resin powder | X |
| Cellulose powder | X |
| Starch powder | X |
| talc powder | X |
| Cross linked-type silicone powder | X |
| PMMA powder | X |
| Barium sulfate powder | X |
| Cross linked-type silicone powder | X |

As is clear from the results in Tables 4 and 5, the prevention and inhibition effects of red discoloration could not be achieved by powder components other than silica.

Example 4

Water-in-oil type emulsion sunscreen cosmetics of the compositions shown in Tables 6 and 7 were prepared according to the normal method. The prevention and inhibition effects of discoloration were evaluated for these samples according to the above-described evaluation criteria. The results are shown in Tables 6 and 7.

In Tables 6 and 7, "(13) hydrophobized (silane treatment)/cation-treated zinc oxide"[*3] with a specific surface area of about 50 $m^2$/g, "(14) hydrophobized (silane treatment)/cation-treated zinc oxide"[*4] with a specific surface area of about 50 to 70 $m^2$/g, and "(15) hydrophobized (silane treatment)/cation-treated zinc oxide"[*5] with a specific surface area of about 70 $m^2$/g were used, respectively. The percentages (mass ratio) of component (b) and component (c) contained in components (13), (14), and (15) were about 98% by mass and about 2% by mass, respectively.

The percentages (mass ratio) of component (b) and component (d) in "(17) hydrophobized (silane treatment)/silica-coated zinc oxide [component (b)+component (d)]" were about 80% by mass and about 20% by mass, respectively.

The percentage (mass ratio) of component (d) in "(18) hydrophobized (silane treatment)/titanium dioxide [component (d)]" was about 10% by mass. That is, the blending amount of component (d) contained in sample 7, shown in Table 7, was 1.5% by mass, and the blending amount of component (d) contained in sample 11 was 0.5% by mass.

TABLE 6

|  | Control | Sample 1 | Sample 2 | Sample 3 | Sample 4 | Sample 5 |
| --- | --- | --- | --- | --- | --- | --- |
| (1) Ion-exchanged water | Balance | Balance | Balance | Balance | Balance | Balance |
| (2) Organic-modified clay minerals | 0.1 | 0.1 | 0.1 | 0.1 | 0.1 | 0.1 |
| (3) Dynamite glycerol | 3.0 | 3.0 | 3.0 | 3.0 | 3.0 | 3.0 |
| (4) Polyoxyethylene methylpolysiloxane copolymer [component (e)] | 2.0 | 2.0 | 2.0 | 2.0 | 2.0 | 2.0 |
| (5) Distearyldimethylammonium chloride [component (c)] | — | — | — | — | — | — |
| (6) Decamethylcyclopentasiloxane | 20.0 | 20.0 | 15.0 | 20.0 | 20.0 | 20.0 |
| (7) Dimethylpolysiloxane | 10.0 | 10.0 | 10.0 | 10.0 | 10.0 | 10.0 |
| (8) Olefin oligomer | 5.0 | 5.0 | 5.0 | 5.0 | 5.0 | 5.0 |
| (9) Trimethylsiloxysilicate | 5.0 | 5.0 | 5.0 | 5.0 | 5.0 | 5.0 |
| (10) Octyl methoxycinnamate | 10.0 | 10.0 | 10.0 | 10.0 | 10.0 | 10.0 |
| (11) Octocrylene (*1) [component (a)] | 5.0 | 5.0 | 5.0 | 5.0 | 5.0 | 5.0 |
| (12) Hydrophobized (silane treatment) zinc oxide [component (b)] | 15.0 | — | — | — | — | — |
| (13) Hydrophobized (silane treatment)/cation-treated zinc oxide (*3) [component (b) + component (c)] | — | 15.0 | 15.0 | — | — | — |
| (14) Hydrophobized (silane treatment)/cation-treated zinc oxide (*4) [component (b) + component (c)] | — | — | — | 15.0 | 15.0 | — |
| (15) Hydrophobized (silane treatment)/cation-treated zinc oxide (*5) [component (b) + component (c)] | — | — | — | — | — | 15.0 |
| (16) Hydrophobized (fatty acid dextrin treatment) zinc oxide [component (b)] | — | — | 3.0 | — | — | — |
| (17) Hydrophobized (silane treatment)/silica-coated zinc oxide [component (b) + component (d)] | — | — | — | — | — | — |
| (18) Hydrophobized (silane treatment)/silica-coated titanium dioxide [component (d)] | — | — | — | — | — | — |
| (19) Silica powder [component (d)] | — | — | 4.0 | — | 4.0 | — |
| (20) Edetate | Appropriate amount | Appropriate amount | Appropriate amount | Appropriate amount | Appropriate amount | Appropriate amount |
| (21) Phenoxyethanol | 0.5 | 0.5 | 0.5 | 0.5 | 0.5 | 0.5 |
| Prevention and inhibition effects of red discoloration (at 70° C. for 3 days, visual evaluation) | ◯ | X | ◯ | ΔX | ◯ | X |

TABLE 7

|  | Sample 6 | Sample 7 | Sample 8 | Sample 9 | Sample 10 | Sample 11 |
| --- | --- | --- | --- | --- | --- | --- |
| (1) Ion-exchanged water | Balance | Balance | Balance | Balance | Balance | Balance |
| (2) Organic-modified clay minerals | 0.1 | 0.1 | 0.1 | 0.1 | 0.1 | 0.1 |
| (3) Dynamite glycerol | 3.0 | 3.0 | 3.0 | 3.0 | 3.0 | 3.0 |
| (4) Polyoxyethylene methylpolysiloxane copolymer [component (e)] | 2.0 | 2.0 | 2.0 | 2.0 | 2.0 | 2.0 |
| (5) Distearyldimethylammonium chloride [component (c)] | — | — | 0.001 | 0.001 | — | — |
| (6) Decamethylcyclopentasiloxane | 20.0 | 20.0 | 20.0 | 20.0 | 20.0 | 20.0 |
| (7) Dimethylpolysiloxane | 10.0 | 10.0 | 10.0 | 10.0 | 10.0 | 10.0 |
| (8) Olefin oligomer | 5.0 | 5.0 | 5.0 | 5.0 | 5.0 | 5.0 |
| (9) Trimethylsiloxysilicate | 5.0 | 5.0 | 5.0 | 5.0 | 5.0 | 5.0 |
| (10) Octyl methoxycinnamate | 10.0 | 10.0 | 10.0 | 10.0 | 10.0 | 10.0 |
| (11) Octocrylene (*1) [component (a)] | 5.0 | 5.0 | 5.0 | 5.0 | 5.0 | 50 |
| (12) Hydrophobized (silane treatment) zinc oxide [component (b)] | — | — | 15.0 | 15.0 | — | — |
| (13) Hydrophobized (silane treatment)/cation-treated zinc oxide (*3) [component (b) + component (c)] | — | — | — | — | 15.0 | 15.0 |
| (14) Hydrophobized (silane treatment)/cation-treated zinc oxide (*4) [component (b) + component (c)] | — | — | — | — | — | — |
| (15) Hydrophobized (silane treatment)/cation-treated zinc oxide (*5) (component (b) + component (c)) | — | — | — | — | — | — |
| (16) Hydrophobized (fatty acid dextrin treatment) zinc oxide [component (b)] | 15.0 | — | — | — | — | — |
| (17) Hydrophobized (silane treatment)/silica-coated zinc oxide [component (b) + component (d)] | — | — | — | — | 5.0 | — |
| (18) Hydrophobized (silane treatment)/silica-coated titanium dioxide [component (d)] | — | 15.0 | — | — | — | 5.0 |
| (19) Silica powder [component (d)] | — | — | — | 6.0 | — | — |
| (20) Edetate | Appropriate amount | Appropriate amount | Appropriate amount | Appropriate amount | Appropriate amount | Appropriate amount |
| (21) Phenoxyethanol | 0.5 | 0.5 | 0.5 | 0.5 | 0.5 | 0.5 |
| Prevention and inhibition effects of red discoloration (at 70° C. for 3 days, visual evaluation) | ◯ | ◯ | X | ◯ | ◯ | ◯ |

As is clear from the results in Tables 6 and 7 for water-in-oil type emulsion sunscreen cosmetics containing component (a), if component (d) is not blended in the system where component (b) and component (c) are contained, the sample changed into red (samples 1, 3, 5, and 8). If component (d) is blended, however, the discoloration to red could be inhibited (samples 2, 4, 9, 10, and 11). When at least one of component (b) and component (c) was missing, the discoloration to red did not take place either with or without component (d) (samples 6 and 7).

More formulation examples are shown below.

Example 5

Water-in-Oil Type Emulsion Sunscreen Milky Lotion

| (Blending components) | (% by mass) |
| --- | --- |
| (1) Decamethylcyclopentasiloxane | 15 |
| (2) Polyoxyethylene/methylpolysiloxane copolymer | 1 |
| (3) Olefin oligomer | 10 |
| (4) Dimethylpolysiloxane | 10 |
| (5) Octyl methoxycinnamate | 10 |
| (6) Octocrylene | 5 |
| (7) Diethylamino hydroxybenzoyl hexyl benzoate | 2 |
| (8) Phenoxyethanol | 0.5 |
| (9) Fragrance | 0.5 |
| (10) Organic-modified clay minerals | 0.1 |
| (11) Hydrophobized (silane treatment)/cation-treated zinc oxide | 15 |
| (12) Silica powder | 5 |
| (13) Crosslinked-type silicone/network-type silicone block copolymer (KSP 100) | 5 |
| (14) Ion-exchanged water | Balance |
| (15) Glycerin | 3 |
| (16) Edetate | Appropriate amount |

(Production Method)

Components (1) to (9) were mixed and dissolved at room temperature to prepare an oil phase in advance. Subsequently, components (10) to (13) were added, and the mixture was dispersively mixed with a disper. Components (14) to (16) were mixed, dissolved, and gradually added to the oil phase by stirring with a disper. The desired sunscreen milky lotion was obtained by mixing and dissolving to a sufficiently homogeneous state.

Example 6

Water-in-Oil Type Emulsion Sunscreen Milky Lotion

| (Blending components) | (% by mass) |
| --- | --- |
| (1) Decamethylcyclopentasiloxane | 20 |
| (2) Polyoxyethylene/methylpolysiloxane copolymer | 1 |
| (3) Olefin oligomer | 10 |
| (4) Dimethylpolysiloxane | 10 |
| (5) Octyl methoxycinnamate | 10 |
| (6) Octocrylene | 5 |
| (7) Paraben | 0.5 |
| (8) Fragrance | 0.5 |
| (9) Organic-modified clay minerals | 0.1 |
| (10) Hydrophobized (silane treatment)/cation-treated zinc oxide | 15 |
| (11) Hydrophobized (silane treatment)/silica-coated titanium dioxide | 5 |
| (12) Crosslinked-type silicone/network-type silicone block copolymer (KSP 105) | 5 |
| (13) Ion-exchanged water | Balance |
| (14) Glycerin | 3 |
| (15) Edetate | Appropriate amount |

(Production Method)

Components (1) to (8) were mixed and dissolved at room temperature to prepare an oil phase in advance. Subsequently, components (9) to (12) were added, and the mixture was dispersively mixed with a disper. Components (13) to (15) were mixed, dissolved, and gradually added to the oil phase by stirring with a disper. The desired sunscreen milky lotion was obtained by mixing and dissolving to a sufficiently homogeneous state.

Example 7

Water-in-Oil Type Emulsion Sunscreen Cream

| (Blending components) | (% by mass) |
| --- | --- |
| (1) Decamethylcyclopentasiloxane | 20 |
| (2) Polyoxyethylene/methylpolysiloxane copolymer | 3 |
| (3) Cetyl isooctanoate | 10 |
| (4) Dimethylpolysiloxane | 5 |
| (5) Octocrylene | 10 |
| (6) 2,4-bis{[4-(2-ethylhexyloxy)-2-hydroxy]phenyl}-6-(4-methoxyphenyl)-1,3,5-triazine | 0.5 |
| (7) Distearyldimethylammonium chloride | 0.001 |
| (8) Phenoxyethanol | 0.5 |
| (9) Fragrance | 0.5 |
| (10) Organic-modified clay minerals | 2.5 |
| (11) Hydrophobized (silane treatment) zinc oxide | 10 |
| (12) Silica powder | 6 |
| (13) crosslinked-type silicone/network-type silicone block copolymer (KSP 101) | 5 |
| (14) Ion-exchanged water | Balance |
| (15) 1,3-butylene glycol | 2 |
| (16) Edetate | Appropriate amount |

(Production Method)

Components (1) to (9) were mixed and dissolved at 70° C. to prepare an oil phase in advance. Subsequently, components (10) to (13) were added, and the mixture was dispersively mixed with a disper. Components (14) to (16) were mixed, dissolved, and gradually added to the oil phase by stirring with a disper. The desired sunscreen cream was obtained by mixing and dissolving to a sufficiently homogeneous state.

What is claimed is:

1. A method of making a water-in-oil type emulsion sunscreen cosmetic comprising:
    mixing (a) octocrylene, (b) hydrophobized zinc oxide having a coating of (c) cationic surfactant on a surface of the hydrophobized zinc oxide, and (d) silica powder consisting of silicic anhydride to make an oil phase; and
    adding a water phase to the oil phase to make the water-in-oil type emulsion sunscreen cosmetic,
    wherein an amount of the (c) cationic surfactant is 0.5 to 10% by mass with respect to the (b) hydrophobized zinc oxide, and
    an amount of the (d) silica powder is 0.1 to 20% by mass with respect to the cosmetic.

2. The method of claim 1, wherein the amount of the (a) octocrylene is 0.2 to 15% by mass with respect to the cosmetic.

3. The method of claim 1, wherein the amount of the (b) hydrophobized zinc oxide is 0.2 to 30% by mass with respect to the cosmetic.

4. The method of claim 1, further comprising adding 0.01 to 20 by mass of (e) silicone surfactant with respect to the cosmetic to the oil phase.

5. The method of claim 2, wherein the amount of the (b) hydrophobized zinc oxide is 0.2 to 30% by mass with respect to the cosmetic.

6. The method of claim 2, further comprising adding 0.01 to 20% by mass of (e) silicone surfactant with respect to the cosmetic to the oil phase.

7. The method of claim 3, further comprising adding 0.01 to 20% by mass of (e) silicone surfactant with respect to the cosmetic to the oil phase.

8. The method of claim 1, wherein an amount of the (a) octocrylene is 0.5 to 10% by mass with respect to the cosmetic.

9. The method of claim 4, wherein the amount of the (a) octocrylene is 0.5 to 10% by mass with respect to the cosmetic.

10. The method of claim 1, wherein an amount of the (a) octocrylene is 1 to 7% by mass with respect to the cosmetic.

11. The method of claim 1, wherein an amount of the (b) hydrophobized zinc oxide is 1 to 25% by mass with respect to the cosmetic.

12. The method of claim 1, wherein an amount of the (b) hydrophobized zinc oxide is 10.1 to 25% by mass with respect to the cosmetic.

13. The method of claim 1, wherein the (c) cationic surfactant forming the surface coating on the (b) hydrophobized zinc oxide comprises at least one selected from the group consisting of stearyltrimethylammonium chloride, hexadecyltrimethylammonium chloride, tetradecyltrimethylammonium chloride, lauryltrimethylammonium chloride, C12 monohydroxyalkylether cation, dihydroxyalkylether cation, cocodiamidopropyl cation, cocodicarboxyethyl cation, C16 dicarboxyethyl cation, C18 dicarboxyethyl cation, POP(15) diethylmethyl cation, POP(25) diethylmethyl cation, POP (40) diethylmethyl cation, C12 diamidopropylmethylamine, C14 diamidopropylmethylamine, C16 diamidopropylmethylamine, C18 diamidopropylmethylamine, iso-C18 diamidopropylmethylamine, di-C18 propyldimethyl cation, hydroxypropyl-bis-lauryl cation, hydroxypropyl-bis-stearyl cation, hydroxypropyl-bis-laurylamide cation, hydroxypropyl-bis-stearylamide cation, C18 monohydroxyalkylether cation, bis-C18 hydroxyalkylether cation, C22 trimethylammonium bromide, C22 propyldimethylamine, quaternium-91, C22 trimethylammonium methosulfate, dicocoylamidoethylethylhydroxy cation, di-C18 amidoethylethylhydroxy cation, di-C16 amidoethylethylhydroxy cation, di-C18 dimethylammonium salt, C18 dimethylbenzylammonium salt, perfluorotrimethylammonium salt, and diacylamidoethylethylhydroxy cation.

14. The method of claim 1, wherein the (d) silica powder has a shape selected from a group consisting of a spherical shape, plate-like shape, particulate shape, and rod-like shape.

* * * * *